United States Patent [19]

Cringle

[11] Patent Number: 4,874,237
[45] Date of Patent: Oct. 17, 1989

[54] ELECTRORETINOGRAM APPARATUS

[75] Inventor: Stephen J. Cringle, Hillarys, Australia

[73] Assignee: Lions Eye Inst. of Western Australia, Nedlunds, Australia

[21] Appl. No.: 190,755

[22] Filed: May 5, 1988

[30] Foreign Application Priority Data

May 7, 1987 [AU] Australia .................................. PI1790

[51] Int. Cl.$^4$ ........................... A61B 3/10; A61B 5/04
[52] U.S. Cl. .................................. 351/221; 351/205; 128/639
[58] Field of Search ............... 351/212, 205, 219, 226, 351/221, 243; 128/639

[56] References Cited

U.S. PATENT DOCUMENTS 4,131,113  12/1978  Fender et al. ..................... 351/212
4,386,831  6/1983  Grounauer ......................... 351/221

OTHER PUBLICATIONS

Cringle et al., Current Eye Research, vol. 5, No. 12, pp. 959–965, (1986).
Cringle et al., Current Eye Research, vol. 6, No. 9, pp. 1109–1114, (1987).
Cringle et al., Clin. Vision Sci., vol. 00, No. 0, pp. 1–7, (1988).

Primary Examiner—Rodney B. Bovernick
Assistant Examiner—P. M. Dzierzynski
Attorney, Agent, or Firm—Kerkam, Stowell & Clarke

[57] ABSTRACT

The invention relates to apparatus and method for taking measurements of the electrical signals from the eye in response to light stimulus which utilizes a plurality of electrodes contacting the sclera of the eye and obtaining outputs of the differences between the signals generated by opposed pairs of electrodes.

8 Claims, 3 Drawing Sheets

ELECTRORETINOGRAM APPARATUS

The present invention relates to an electroretinogram apparatus.

It is known to use an apparatus called an electroretinogram (ERG) as an indicator of retinal function.

Typically, with existing techniques either a brief flash of light or a more complex pattern light stimulus is presented to the eye and the electrical response of the eye is picked up by a first electrode placed on or adjacent the cornea of the eye. A second electrode, which is a reference electrode, is placed elsewhere on the body of the subject such as on the forehead or cheek.

Further, a third electrode may be used for differential recording. This third electrode may be placed on the ear or another extraocular location.

Information obtained from both the amplitude and the latency of signal components recorded is used in the diagnosis and monitoring of various retinal diseases. However, it has been found that the known techniques suffer from various problems.

For example, the amplitude of the ERG even for a normal eye is subject to considerable variation between experiments. Between different patients the variations may be even larger. This variability has limited the effectiveness of electroretinography in diagnosing the presence of local areas of retinal malfunction which may produce only a subtle reduction in the total ERG.

Further, with the use of only a single electrode on the surface of the eye there is no information obtained about the distribution of ERG potential around the eye. It has now been discovered that the distribution of ERG potentials is significantly altered by the presence of a retinal lesion.

Still further, a contact with the eye is generally made with the cornea using a contact lens or a foil or wire. However, the cornea is very sensitive to touch and patient comfort is often a limiting factor in success of a measurement. Vision may also be obstructed by a corneal contact system, which may be a problem with pattern electroretinography in which clear optical pathways are required.

Yet, still further, extraneous noise from electrical pickup and muscular activity has to be eliminated by signal averaging techniques. This sometimes requires a large number of repetitive measurements.

The present invention provides an apparatus for the measurement of electrophysiological signals used in the diagnosis of retinal disease in both man and animals in which one or more of the problems outlined above is alleviated. In particular, the apparatus of the present invention has utility in the provision of information about the magnitude and location of a retinal lesion.

In accordance with one aspect of the present invention there is provided an electroretinogram apparatus for taking measurements of signals from an eye in response to stimulus which comprises a first reference electrode arranged to be electrically connected to a part of the body and a plurality of second scleral electrodes arranged to be distributed about the sclera away from the cornea, means for simultaneously recording the amplitude of signals from the plurality of second scleral electrodes and means for recording differences between opposed pairs of electrodes of the plurality of second scleral electrodes.

In accordance with another aspect of the present invention there is provided a method of measuring signals from an eye in response to stimulus which comprises contacting a plurality of electrodes with the sclera in a spaced apart relationship, providing a light stimulus to the eye so as to produce an electrical output at each electrode, feeding the electrical outputs from opposed pairs of electrodes to difference calculating means so as to calculate the differences in the magnitude of the opposed outputs and providing a net output representative of the differences.

The present invention will now be described, by way of example, with reference to the accompanying drawings, in which.

It has been found that a normal distribution of voltage signal amplitudes measured between a fixed electrode on the cornea and a movable electrode on the sclera has a near zero amplitude over the first few millimetres of the sclera moving towards the optic nerve followed by a rapid voltage signal growth until a maximum is attained at the optic nerve/scleral boundary. The signal distribution is distributed symmetrically about the axis of the eye. This phenomenon has been described in detail in a number of papers including "The effect of scleral recording location on ERG amplitude" Current Eye Research 5, 959–965 by Cringle, Alder, Yu and Brown and "The effect of a retinal lesion on the distribution of b wave amplitudes on the sclera" Current Eye Research 6 1109–1114 by Cringle and Alder.

Figure 1:
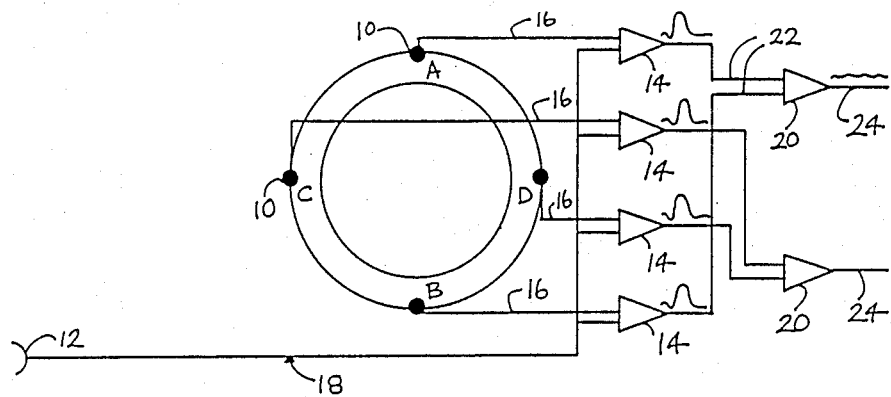
FIG. 1 shows an apparatus comprising an electrode array and amplifier system which records ERG from a number of scleral electrodes and then compares them to measure the asymmetry of the ERG distribution on the sclera.
Figure 2:
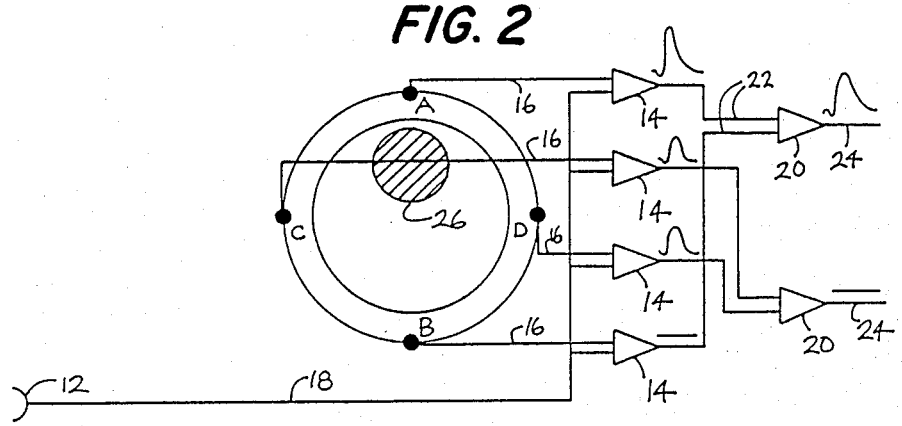
FIG. 2 shows an apparatus as in FIG. 1 in use with an eye containing a retinal lesion.

It has now been found that the presence of retinal lesions distorts the signal distribution into an asymmetrical form. In FIGS. 1 and 2 of the drawings there is shown an electroretinogram apparatus comprising an electrode array 10 having electrodes A,B,C and D which may be built into a scleral fitting annulas. Alternatively, the electrodes may be individually placed on the sclera of an eye.

As shown, a typical electrode format would have four electrodes disposed at 90° to one another about the corneal limbus. The electrodes A, B, C and D are arranged to contact the sclera in radially spaced apart manner at substantially the same axial distance from the cornea. A reference electrode 12 is arranged to be connected to a remote location such as the forehead or cheek of the patient.

The electrodes A to D are connected to positive terminals of respective conventional amplifiers 14 via lines 16. The reference electrode 12 is connected to negative terminals of the amplifiers 14 via a line 18. ERG signals from the electrodes A to D are recorded simultaneously using the amplifiers 14. These signals are further processed by passing the amplified signals from opposed electrodes to difference amplifiers 20 via lines 22.

In use, an eye in contact with the electrodes A, B, C, D located at substantially the same axial distance from the cornea is exposed to a light stimulus which produces simultaneous signals from all of the electrodes. In a normal eye the symmetrical nature of the signal distribution will result in all channels having similar outputs and the resultant difference signals from the difference amplifiers 20 output along lines 24 will be close to zero. This is shown in FIG. 1.

However, if there is a retinal lesion 26 affecting one of the scleral electrodes as illustrated in FIG. 2, then one of the outputs along line 24 will be close to zero whilst the other will have an amplitude which is either positive or negative depending on which electrode is adjacent the lesion and the magnitude of the lesion. This is shown in FIG. 2.

Similarly, if there is a retinal lesion between two adjacent electrodes then both of the outputs along the lines 14 will have a positive or negative amplitude depending on which part of the eye is affected and the magnitude of the lesion. The plurality of the responses from the difference amplifiers enables an operator to ascertain the location of the lesion.

Figure 3:
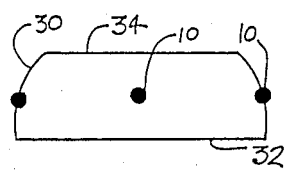
FIG. 3 is a side elevation of a scleral cap which may form part of the apparatus of FIGS. 1 and 2.
Figure 4:
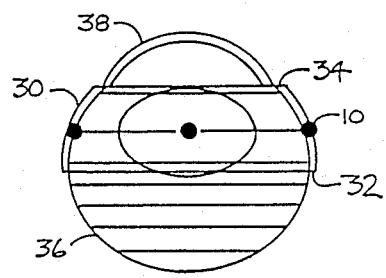
FIG. 4 is a side elevation of the scleral cap of FIG. 3 mounted on an eye.
Figure 5:
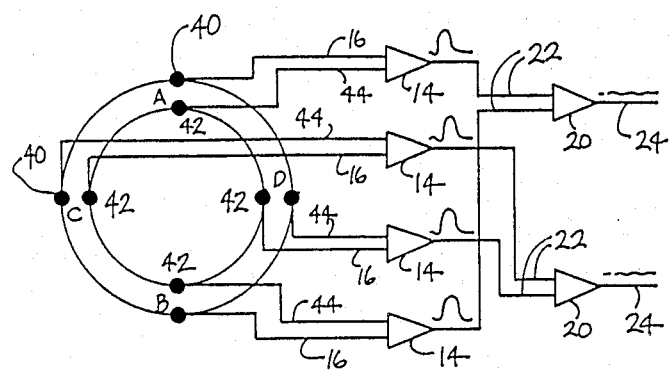
FIG. 5 shows an apparatus comprising an electrode array and amplifier system similar to that of FIGS. 1 and 2 but with a modified arrangement of reference electrode.
Figure 6:
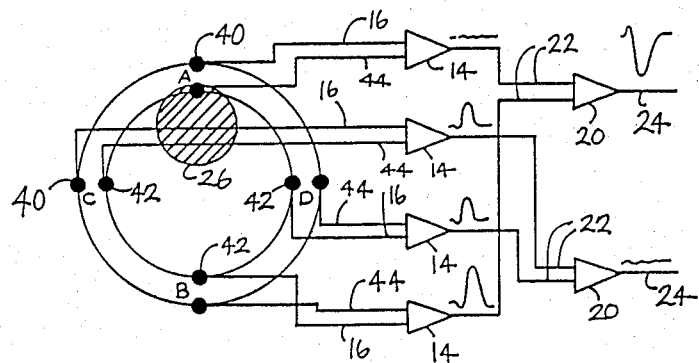
FIG. 6 shows an apparatus as in FIG. 5 in use with an eye containing a retinal lesion.

The electrode array 10 may be conveniently fitted into a scleral fitting apparatus as shown in FIG. 3. The apparatus of FIG. 3 comprises a flexible annular cap 30 of approximately the same curvature as the sclera and having a first wide open end 32 and a second narrow open end 34. The electrodes A to D of the array 10 are embedded into the inner face of the annulus between the ends 32 and 34 as shown in FIG. 3. As can be seen in FIG. 4, the annular cap 30 is readily placed onto an eye 36 with the wide end 32 formost until the cap 30 engages snugly with the sclera. As can be seen in FIG. 4, in this position cornea 38 of the eye 36 is unobstructed by the cap 30. In FIGS. 5 and 6 of the drawings there is shown an electroretinogram apparatus comprising an electrode array 40 having electrodes A, B, C and D.

The apparatus is similar to that shown in FIGS. 1 and 2 and like reference numerals denote like parts.

However, the reference electrode 12 is replaced by a plurality of respective reference electrodes 42 for each of the electrodes A, B, C and D. Each reference electrode 42 is connected by a line 44 to the positive terminal of the amplifier corresponding to the respective electrode A, B, C and D.

In this arrangement the active electrodes A, B, C and D and the reference electrodes 42 are placed close together as the reference electrodes 42 are located at the corneal limbus whilst the active electrodes are located further back on the sclera. This arrangement has the advantage of reducing the pickup of extraneous signals between the active and reference electrodes since, as well as being closer together, there is no muscle activity between them. In other aspects the apparatus of FIGS. 5 and 6 apparatus operates in the same manner as the apparatus of FIGS. 1 and 2, as described hereinabove.

Figure 7:
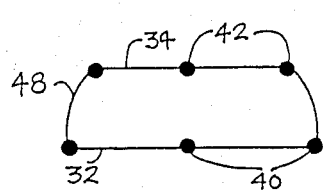
FIG. 7 is a side elevation of a scleral cap which may form part of the apparatus of FIGS. 5 and 6.

Further, the electrode array 40 may be conveniently fitted into a scleral fitting annulas as shown in FIG. 7.

Figure 8:
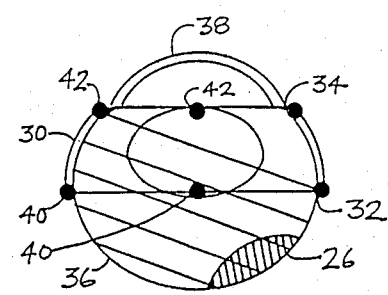
FIG. 8 is a side elevation of the scleral cap of FIG. 7 mounted on an eye.

The apparatus of FIG. 7 comprises a flexible annular cap 48 similar to that shown in FIG. 3 and like reference numerals denote like parts. As with the cap 30 of FIG. 3, the cap 48 of FIG. 7 fits over an eye as shown in FIG. 8.

The use of a plurality of scleral electrodes in the present invention has the advantage of reducing background noise since this is common to all electrodes and the recording is differential. Further, it is not essential to contact the cornea. This avoids compromising vision through the cornea.

Further, as the scleral electrodes may be placed adjacent the equatorial region of the sclera the recorded signal amplitudes may be greater than those recorded conventionally because of the high rate of growth of signal amplitude in the equatorial region of the sclera. This may reduce the need for signal averaging and improve the signal to noise ratio obtainable.

Figure 9:
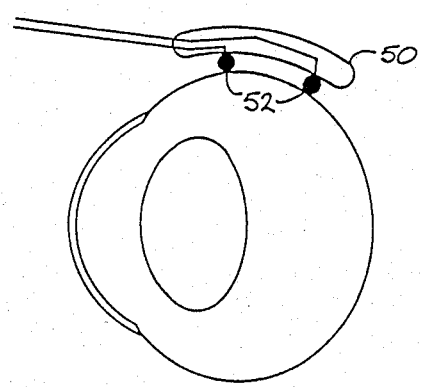
FIG. 9 shows a side elevation of a device containing a pair of electrodes only for measuring ERG.

The device of FIG. 9 could be incorporated into any single channel electrophysiological system and provide an improvement in patient comfort and electrical noise immunity compared to existing devices.

The device of FIG. 9 comprises a flexible cap having a pair of electrodes fitted on its underside. The electrode pair is separated by a fixed distance. Further, the cap has a curvature approximately the same as that of the sclera. The device of FIG. 9 enables ERG potential differences from point to point on the sclera to be recorded.

Figure 10:
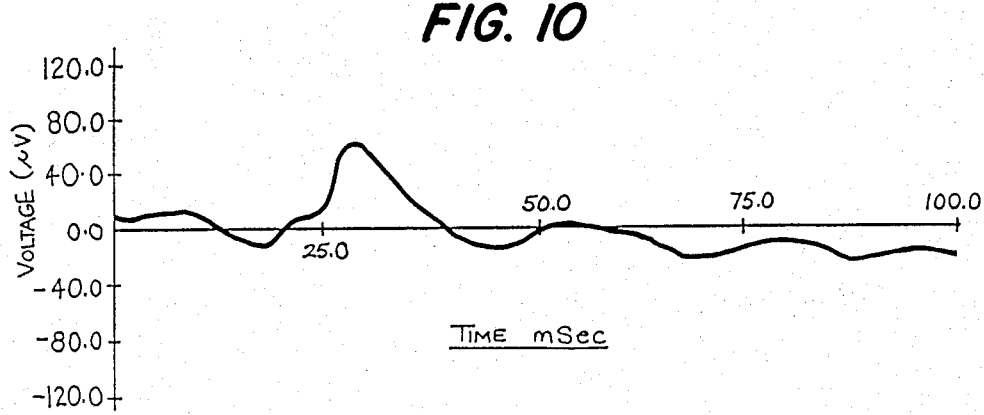
FIG. 10 is a view of a photopic ERG human obtained using the device of FIG. 9.

Results of preliminary trials on human ERG detection using the cap 50 of FIG. 9 are presented in FIG. 10. The photopic ERG of FIG. 10 was recorded using a standard clinical electrophysiology system, by using scleral electrodes 10mm apart in a scleral cap of the type shown in FIG. 9.

With a simple flash ERG stimulus and an electrode array objective information about the size and location of a retinal lesion can be obtained using the apparatus shown in FIGS. 1 to 8. With a pattern stimulus it would be possible to detect and quantify any non uniform loss of ganglion cell or nerve fibre function as may occur in the early stages of glaucoma.

Thus, the apparatus of the present invention may have application as a screening aid in the detection of the early effects of glaucoma.

Modifications and variations such as would be apparent to a skilled addressee are deemed within the scope of the present invention. For example, the reference electrodes 42 could be replaced by a single ring reference electrode arranged to contact the eye adjacent the corneal limbus. Also, the number of electrodes could be increased to improve the spatical resolution of lesion localisation.

I claim:

1. An electroretinogram apparatus for taking measurements of signals from a person's eye in response to stimulus which comprises a first reference electrode arranged to be electrically connected to a part of the person's body and a plurality of second scleral electrodes arranged to be distributed in spaced apart manner, about the sclera away from the cornea, means for simultaneously recording the amplitude of signals from the plurality of second scleral electrodes and means for recording differences between opposed pairs of electrodes of the plurality of second scleral electrodes thereby allowing the determination of the magnitude and location of a lesion that may be present in the eye.

2. An apparatus according to claim 1, in which the first reference electrode is arranged to contact the eye adjacent the cornea.

3. An apparatus according to claim 2, in which the first reference electrode comprises a plurality of first electrodes each corresponding with a respective scleral electrode.

4. An apparatus according to claim 3, in which the first and second electrodes are embedded in an interior face of an annular scleral cap arranged to fit snugly over the sclera, each first reference electrode being located adjacent its respective second scleral electrode.

5. An apparatus according to claim 1, in which the first reference electrode is arranged to be connected to a forehead or cheek.

6. An apparatus according to claim 5, in which the second scleral electrodes are embedded in an interior face of an annular scleral cap arranged to fit snugly over the sclera.

7. An apparatus according to claim 1, in which each scleral electrode is electrically connected to an amplifier which is also connected to the reference electrode, and each amplifier output is arranged to be fed to a difference amplifier which is also arranged to receive the amplifier output from the amplifier of an opposed electrode so as to produce a difference signal.

8. A method of measuring signals from a person's eye in response to stimulus which comprises contacting a plurality of electrodes with the sclera of the eye in spaced apart relationship, providing a light stimulus to the eye so as to produce an electrical output at each electrode, feeding the electrical outputs from opposed pairs of electrodes to difference calculating means so as to calculate the differences, if any, in the magnitudes of the opposed outputs and providing a net output representative of the differences.

* * * * *